United States Patent [19]

Lichstein et al.

[11] Patent Number: 4,536,178
[45] Date of Patent: Aug. 20, 1985

[54] TAMPON APPLICATOR

[75] Inventors: Bernard Lichstein, Elizabeth, N.J.; Michael Handler, Norwalk, Conn.

[73] Assignee: International Playtex, Inc., Stamford, Conn.

[21] Appl. No.: 550,684

[22] Filed: Nov. 10, 1983

[51] Int. Cl.³ .................................................. A61F 15/00
[52] U.S. Cl. ..................................................... 604/15
[58] Field of Search .................................... 604/11–18

[56] References Cited

U.S. PATENT DOCUMENTS

| | | |
|---|---|---|
| 2,587,717 | 3/1952 | Fourness . |
| 3,059,642 | 10/1962 | Gershen . |
| 3,068,867 | 12/1962 | Bletzinger et al. . |
| 3,086,527 | 4/1963 | Forrest . |
| 3,090,385 | 5/1963 | Brecht . |
| 3,103,929 | 9/1963 | Brecht . |
| 3,124,134 | 3/1964 | Gardner . |
| 3,351,060 | 11/1967 | de Woskin . |
| 3,409,011 | 11/1968 | Mittag ................................. 604/15 |
| 3,575,169 | 4/1971 | Voss et al. . |
| 3,645,263 | 2/1972 | Bates . |
| 3,805,786 | 4/1974 | Bernardin et al. . |
| 3,807,399 | 4/1974 | Mooman et al. ..................... 604/14 |
| 3,831,605 | 8/1974 | Fournier . |
| 3,835,856 | 9/1974 | Warncke . |
| 3,895,634 | 7/1975 | Berger et al. . |
| 4,269,187 | 5/1981 | Sakurai ................................. 604/14 |
| 4,318,405 | 3/1982 | Sneider . |

FOREIGN PATENT DOCUMENTS

| | | | |
|---|---|---|---|
| 121844 | 8/1946 | Australia ................................. 604/18 |
| 700840 | 12/1964 | Canada ................................. 604/11 |

Primary Examiner—John D. Yasko
Assistant Examiner—Christa K. Scott
Attorney, Agent, or Firm—Stewart J. Fried

[57] ABSTRACT

A tampon applicator includes a tubular barrel adapted to house a tampon therein and accommodate a slidable, tubular plunger which is adapted to push the tampon within the barrel out of the forward end of the barrel into a vagina. The barrel includes a rear portion having two diametrically opposed, substantially flattened surfaces with gripping ribs thereon and an angled transitional shoulder which has a reduced diameter relative to the front portion of the barrel. The flattened surface and the angled shoulder form a thumb and finger hold which enables a user to securely and comfortably maneuver and position the applicator and tampon therein.

14 Claims, 6 Drawing Figures

TAMPON APPLICATOR

BACKGROUND OF THE INVENTION

1. Field of the Invention

The invention relates to catamenial devices for introducing catamenial tampons into the vaginal cavity and, more particularly, to a tampon applicator which is constructed in a manner to facilitate its use.

2. Description of the Related Art

Catamenial tampons have been replacing sanitary napkins in preference among large numbers of women due to its ease of use and lack of restriction. In particular, since a tampon is worn internally, its size and shape necessarily permit easy insertion or removal. Proper placement of the tampon within the vagina is extremely important in an effort to maximize leakage protection and comfort.

Three general methods of tampon insertion are typically used. The first involves the use of a tampon inserter or applicator consisting of a hollow cylinder having openings at both ends. A slidable, telescoping plunger is provided through one open end for ejecting the tampon through the opposite end after the cylinder has been placed within the vagina. The applicator and its plunger are removed from the vagina after the tampon has been ejected. The second method involves the use of a rigid inserter attached to the base of the tampon. The inserter is pulled away after it is used to insert the tampon. The third method involves direct placement of the tampon within the vagina with one's finger. The present invention relates to the first of these methods of insertion.

Tampon inserters or applicators are generally well known in the prior art. Typically, the applicators of the first method described above are comprised of telescopically slidable inner and outer tubes with a tampon being positioned along the inside of the outer tube and the inner tube being positioned beneath the base of the tampon. The tampon is expelled from the outer tube by moving the inner tube longitudinally within the outer tube in the direction of the tampon. The outer tube is typically formed from cardboard or plastic. The tampon itself is generally an elongated cylinder of compressed absorbent material and has a removal string which, upon placement within the applicator, extends out of the back of the outer tube through an opening therein.

Various configurations for the outer tube or container and inner tube or ejection means have been proposed to facilitate manufacture, handling and placement of the applicator as well as ejection of the tampon. These have included forming the applicator components from materials having different physical properties and varying the size and shape of the applicator components or tampons. The prior art developments most closely related to the present invention involve the various constructions with respect to the applicator including the container and ejection means.

For example, U.S. Pat. No. 3,124,134 to Gardner, issued Mar. 10, 1964, discloses a tampon applicator having a cylindrical sleeve which includes a reduced diameter portion 25 and transition portion 22. Although circumferential ribs 26 are provided to improve gripping of the applicator, the applicator is essentially cylindrical and therefore, upon tactile grasp thereof, the applicator permits and promotes at least rotational movement or play, making maneuvering and positioning difficult.

U.S. Pat. No. 3,086,527 to Forrest, issued Apr. 23, 1963, also discloses an applicator that has a tubular barrel, but with an end portion having an arcuate depression which serves as a thumb and finger hold. As with Gardner, significant rotational play still exists due to the relatively cylindrical construction.

Accordingly, no tampon applicator to date has been simply designed to overcome the above-mentioned problem and, thus, provide security, comfort and control for a user.

SUMMARY OF THE INVENTION

In accordance with the invention, a tampon applicator includes a tubular barrel adapted to house and carry a tampon therein and a slidable, tubular plunger telescopically engageable with the barrel and operable to push the inner most end or base of a tampon within the barrel out of the forward end of the barrel into a vagina. The barrel includes a cylindrical front portion adapted to house the tampon and a rear portion adapted to engage the plunger and provide a transition between the rear plunger entry and support area of the barrel and the front portion. The rear portion has two diametrically opposed, substantially flattened surfaces which transcend from two diametrically opposed, angled shoulders. The flattened surfaces and angled shoulders provide a finger and thumb hold or grip which enables a user to comfortably hold the applicator with little or no involuntary rotation and to eject the tampon from the applicator and more accurately control the placement of the tampon.

In a preferred embodiment, the flattened surfaces of the rear portion have a plurality of spaced apart ribs to provide an improved tactile grip. Additionally, an arcuate depression may be provided on the substantially flattened surfaces of the rear portion of the barrel to further complement the finger configuration, aid in comfort of use and enhance the control of the applicator.

To further maximize tactile contact between the user's fingers and the applicator and to accommodate the flattened surfaces of the rear portion of the barrel, the axially engageable plunger preferably has a generally rectangular cross-section. The corners of the rectangular cross-section have some radius of curvature to reduce any untoward frictional contact with the inner surfaces of the rear portion and to enhance the aesthetic qualities of the device.

The applicator construction is further preferably provided with guide means to axially guide the plunger within the rearward portion of the barrel. The guide means preferably includes a plurality of ridges or protrusions on the inner tubular surface of the rear portion which are axially engageable with and along the length of the outer tubular surface of the plunger.

It has been shown as a result of extensive testing with the applicator in accordance with this invention that the finger and thumb hold or grip of the applicator has a significantly greater surface contact area (finger/applicator interface) in comparison to a conventional applicator having a relative cylindrical barrel. Further, it has been shown that the applicator in accordance with this invention significantly reduces the amount of involuntary rotation and, thereby, lack of control during insertion in comparison with use of a conventional applicator having a cylindrical barrel. Additionally, it has been noted that the applicator in accordance with the invention provides a consumer perceptable, enhanced feeling of security, comfort and control which is theorized to be a result of a reduced level of muscle tension required to maneuver the applicator and deploy the tampon from the applicator.

BRIEF DESCRIPTION OF THE DRAWINGS

The invention will now be described with reference to the accompanying drawings in which.

DESCRIPTION OF THE PREFERRED EMBODIMENTS

Figure 1:
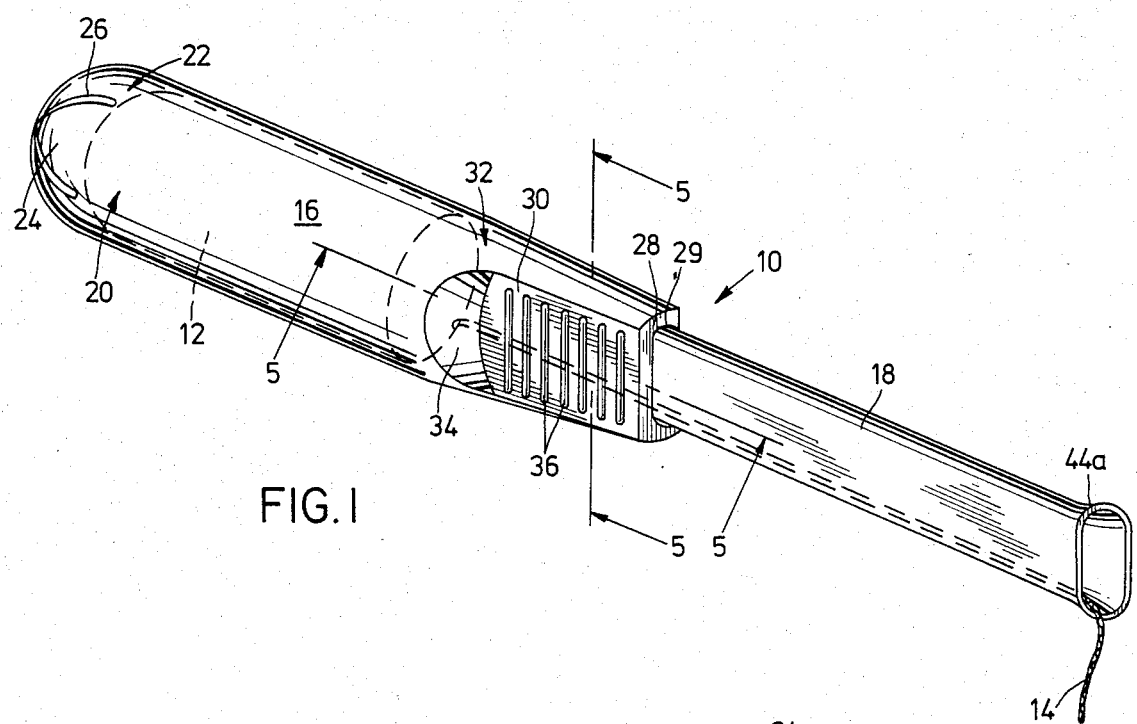
FIG. 1 is a perspective view of the tampon applicator in accordance with the invention.
Figure 6:
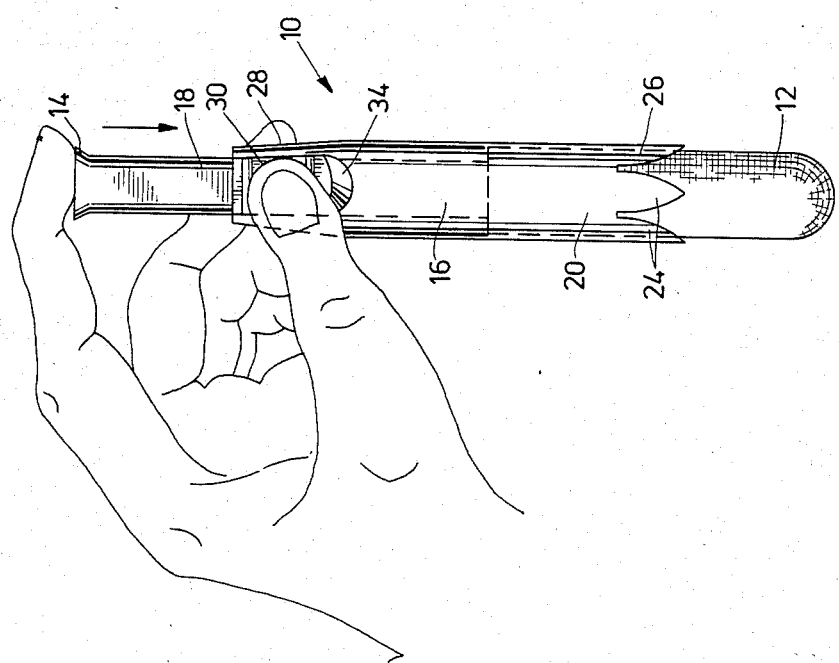
FIG. 6 is a perspective view of the applicator in accordance with the invention with a tampon partially ejected therefrom.
Figure 4:
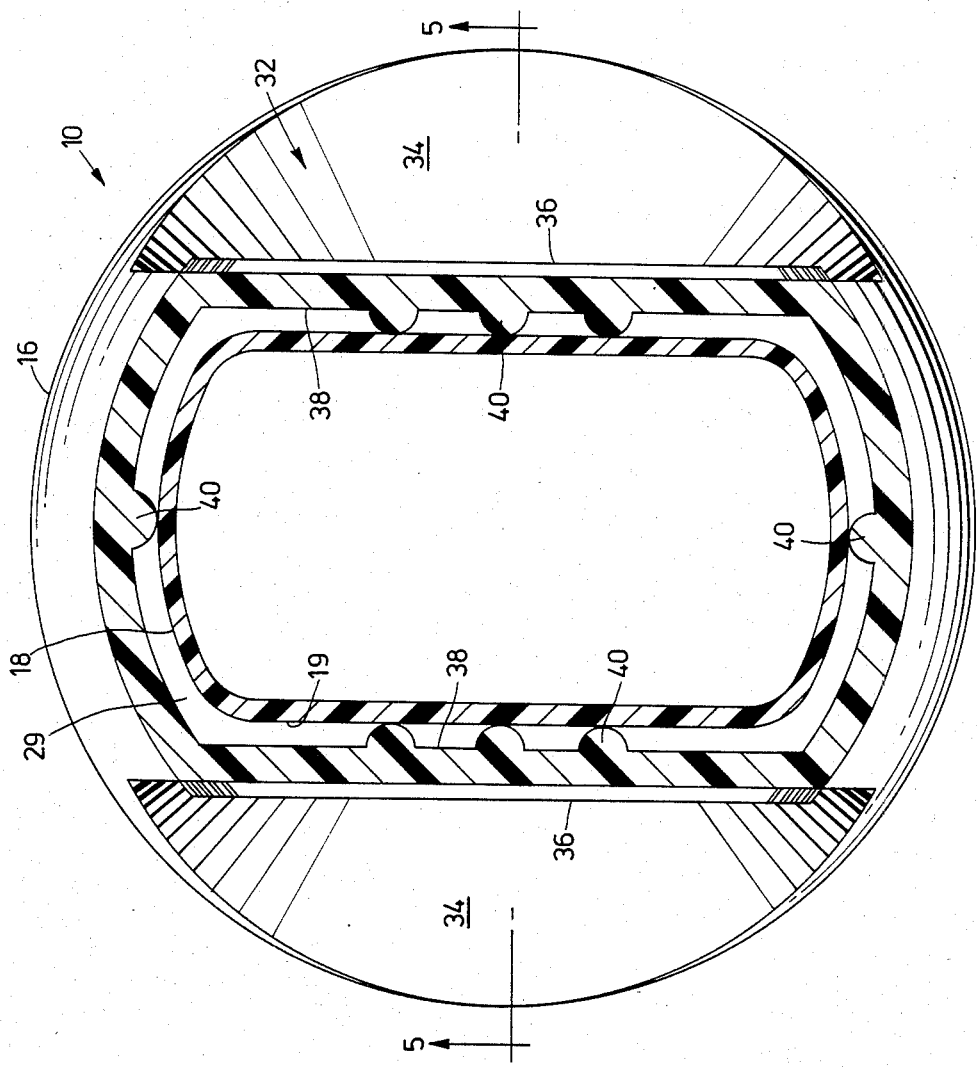
FIG. 4 is an exploded, bottom sectional view of the applicator taken along lines 4—4 in FIG. 2.

As best seen in FIGS. 1 and 6, a tampon applicator or inserter 10 houses and carries a tampon 12 with a removal string 14 for ejection thereof into the vagina of a woman. The applicator 10 includes a slidable, tubular plunger 18 telescopically engageable with a barrel 16. The barrel 16 is tubular and adapted to house and carry the tampon 12 therein. The plunger 18 is adapted to push or eject the innermost end of the tampon 12 in the barrel 16 out of the forward or front portion 20 of the barrel 16 into the vagina of a user. The barrel 16 and plunger 18 are specially constructed to enhance security, comfort and control in maneuvering and positioning the applicator 10 and the tampon 12.

Figure 2:
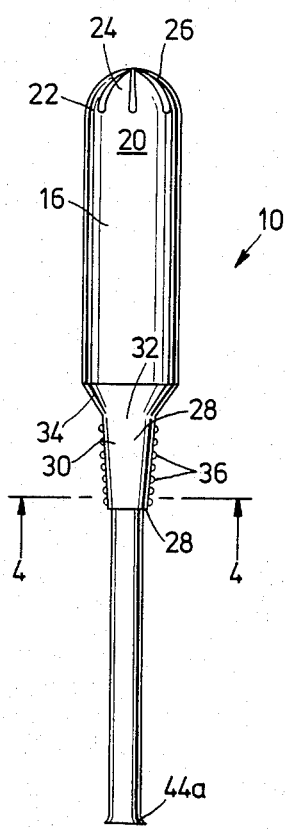
FIG. 2 is a side elevational view of the applicator in FIG. 1.
Figure 3:
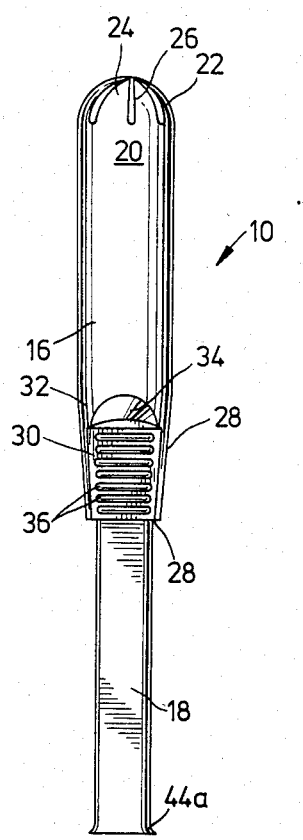
FIG. 3 is a front elevational view of the applicator in FIG. 1.

With reference to FIGS. 2 and 3, it can be seen that the barrel 16 includes a front cylindrical portion 20 and a rearward tubular portion 32. The front cylindrical portion 20 holds the tampon 12 therein and permits the tampon 12 to be ejected or passed therefrom through an hemispherical, dome-shaped tip 22. The tip 22 includes a plurality of petals 24 which are formed by a plurality of slits 26. The petals 24 are flexible enabling the tampon 12 to be ejected therethrough when the plunger 18 is pressed against the top of the tampon 12 within the barrel 16.

The rearward portion 32 has a decreasing or tapered diameter relative to the front portion 20 which serves as a transition between the front portion 20 and a rearward plunger entry and support area 28. The rearward portion 32 including two generally flattened surfaces 30 and two angled shoulder surfaces 34 also forms a novel finger and/or thumb hold or grip. As best seen in FIG. 6, a user preferably places her middle finger and thumb on the flattened surfaces 30 with the tip and side surfaces of the finger and thumb resting against the angled shoulders 34. The index finger of the same hand or of the other hand is rested against the bottom of the plunger 18 and is used to push the plunger 18 forward and thereby eject the tampon 12 after the applicator 10 has been inserted. Thus, the flattened surfaces 30 provide a grasp area while the angled shoulders 34 provide a push area for the finger and thumb. In total, the rear portion 32 provides a secure hold or grip which enables the user to securely and comfortably maneuver and control the applicator barrel 16.

The angled shoulders 34 transcend from the cylindrical front portion 20 to the flattened surfaces 30 and, thus, have a reduced diameter relative to the front portion 20. The angled surface of the shoulders 34 can vary from almost 0° to almost 90° relative to the length of the barrel 16. Accordingly, the angled shoulder surfaces 34 of the rear portion 32 provide an area on which the middle finger and thumb of a user may push off or rest on during the grasping of the applicator 10 and insertion of the applicator 10 and tampon 12 into the vagina of a user.

To further enhance grasping of the barrel 16, the two generally flattened surfaces 30 are generally decreasingly tapered from the angled shoulders 34 to the plunger entry area 28. Additionally, a plurality of spaced apart ribs or treads 36 are provided on the surfaces 30. Although the ribs or treads 36 are configured in a straight and raised design, a stepped and/or curved design may be alternatively selected. The surfaces 30 may also be provided with a concavity or arcuate depression (not shown) configured to complement the curvature of a user's fingers. Thus, by providing the rear portion 32 of the barrel 16 with a generally flat, tapered configuration and with grasping ribs 36, the rear portion 32 of the barrel 16 serves as a grasping area for the middle finger and thumb.

The rear portion 32 is generally rectangular in cross-section to accommodate the flattened surfaces 30 thereof. Alternative cross-sectional shapes may be selected as long as such cross-sections accommodate the generally flattened surfaces 30 of the rear portion 32. Further, it should be understood that the cross-sectional areas of either end of the rear portion 32 do not necessarily need to be the same. For example, the examples shown in the figures have continued decreasing cross-sections from one end to the other. In addition, the cross-sections may reflect any concavities provided on the outer flattened surfaces 30 of the rear portion 32.

The rear portion 32 is also constructed to receive and axially engage the plunger 18 through an opening 29 therein. Accordingly, the general cross-sectional configuration of the rear portion 32 and the plunger entry area 28, in particular, are preferably similar or comparable to that of the plunger 18 to accommodate smooth axial engagement between the barrel 16 and the plunger 18. Further, as in the preferred embodiment, the corners of the rectangular cross section of the rear portion 32 have some radius of curvature which reduces any untoward frictional contact of the plunger 18 with the outer surfaces of the rear portion 28 and to enhance the aesthetic appearance of the applicator 10.

Figure 5:
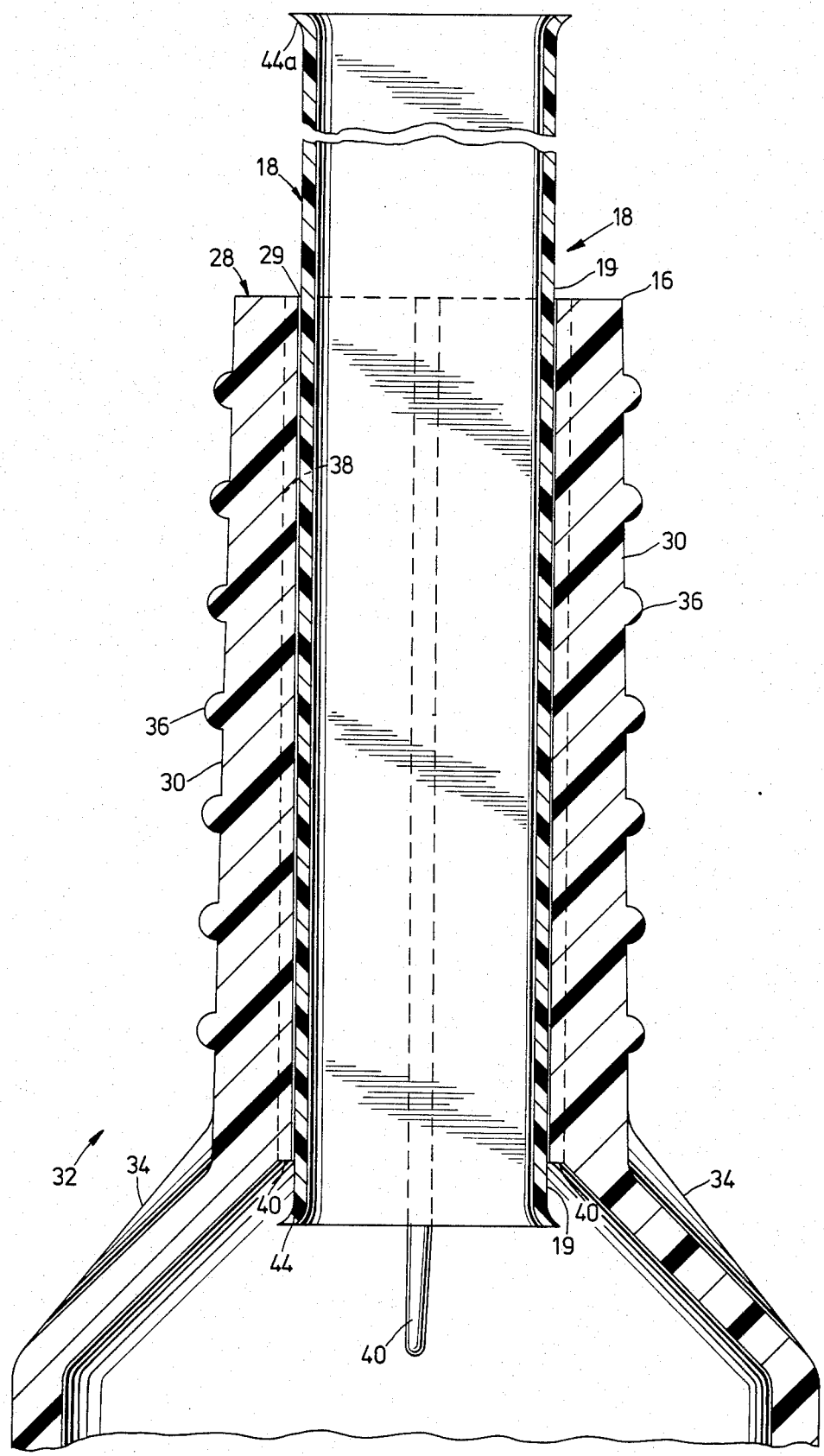
FIG. 5 is a partial, exploded, side sectional view of the applicator taken along lines 5—5 of FIG. 4.

To further assure smooth axial engagement of the plunger 18 through and into the rear portion 32 of the barrel 16, an inner surface 38 of the rear portion 32 is provided with ridges or protrusions 40 which are adapted to engage exterior surfaces 19 of the plunger 18. As best seen in FIG. 5, these ridges 40 run the length of the interior of the rear portion 32 of the barrel 16. Accordingly, the ridges 40 provide a means for guiding the plunger 18 axially within the rearward portion 32 of the barrel 16.

The plunger 18 may additionally include means for limiting the movement of the plunger 18 through the rearward portion 32 of the barrel 16. One manner of limiting the movement of the plunger 18 is by providing at least one curled lip 44 integral with the inner end of the plunger 18 and engageable with the angled shoulders 34 and preferably a second curled lip 44a integral with the outer end of the plunger 18 and engageable with the plunger entry area 28 of the barrel 16. The second curled lip 44a additionally provides a comfortable surface for resting the index finger in pushing the plunger 18 forward to eject the tampon 12. The outer end of the plunger 18 may have other collar-like members or configurations such as an oval, circular cross-section or an arcuate finger rest which function in like manner as the curled lip 44a.

As best seen in FIG. 6, tampon insertion takes place with the aid of the applicator 10 in accordance with the invention by pushing the plunger 18 through the barrel 16 in contact with the tampon 12 to deploy the tampon 12 from the barrel 16 into a user's vagina. This deployment is performed almost entirely with tactile sense and under a wide range of diverse conditions and personal technique. However, as stated above, a typical user uses a minimum of three fingers to deploy the tampon and, in particular, usually uses the thumb and middle finger to grasp and manipulate the barrel 16 and the index finger to push the plunger 18 through the barrel 16. During the pushing of the plunger 18 into the barrel 16 and insertion and deployment of the tampon 12 from the applicator 10 into the vagina, increased grip pressure must be applied to the barrel 16. With the middle finger and thumb hold of the present invention, application of increased grip pressure does not cause any instability as in the prior art applicators wherein rotational or lateral slip or play between the applicator barrel and the fingers results from grasping the applicator barrel. On the contrary, the finger and thumb hold construction of the present invention enhances stability in maneuvering and positioning the applicator 10 and ejection and placement of the tampon 12. Accordingly, the tampon applicator 10 of this invention reduces or eliminates any slip or play, thereby reducing muscle tension. Thus, a user of the applicator 10 is provided with added security, comfort and control.

In summary, a woman can securely and comfortably grasp, control and position a tampon applicator 10 in accordance with this invention and a tampon 12 housed therein as a result of the finger and thumb hold or grip formed by the angled shoulders 34 and flattened surfaces 30 of the rear portion 32 of the applicator 10. By placing the user's middle finger and thumb on the flattened surfaces 30 of the rear portion 32 of the barrel 16 and set against the angled shoulders 34 of the barrel 16, the user is able to easily maneuver, control and position a tampon within her vagina without any excess muscle tension or strain which may result, in part, from rotational or lateral instability and movement.

The foregoing specification and drawings are merely illustrative of the invention and are not intended to limit the invention to the disclosed embodiment. Variations and changes which are obvious to one skilled in the art are intended to be within the scope and nature of the invention which are defined in the appended claims.

The embodiments of an invention in which an exclusive property or privilege is claimed are defined as follows:

1. A tampon applicator comprising:
a tubular barrel adapted to house and carry a tampon therein and a slidable, tubular plunger telescopically engageable with said barrel and operable to push the innermost end of the tampon within the barrel out of the forward end of the barrel into a vagina;
said tubular barrel comprising:
(a) a cylindrical front portion adapted to house said tampon;
(b) a rearward portion adapted to partially house and engage said plunger, said rearward portion of said barrel comprising two diametrically opposed, substantially flattened surfaces; and
(c) a transitional section between said rearward portion and said front portion, said transitional section having a reduced diameter relative to said front portion of said barrel;
whereby said flattened surfaces and said transition section provide a finger and thumb hold enabling a user to comfortably eject and control the position of said tampon.

2. The applicator of claim 1 wherein said transitional section comprises two diametrically opposed, angled shoulder surfaces.

3. The applicator of claim 1 wherein said flattened surfaces comprises a plurality of spaced apart ribs.

4. The applicator of claim 1 further comprising means for guiding said plunger axially within said rearward portion of said barrel.

5. The applicator of claim 4 wherein said guide means comprises a plurality of protrusions on an inner tubular surface of said rearward portion of said barrel which are axially engageable with said outer tubular surface of said plunger.

6. The applicator of claim 1 wherein said rearward portion of said barrel has a generally rectangular cross section.

7. The applicator of claim 6 wherein said plunger has a generally rectangular cross section.

8. The applicator of claim 1 wherein said flattened surfaces of said barrel comprises an arcuate depression.

9. The applicator of claim 1 further comprising means for limiting the movement of said plunger through said rearward portion of said barrel.

10. The applicator of claim 9 wherein said limiting means comprises a first curled lip integral with the inner end of said plunger and engageable with said transition portion and a second curled lip integral with the outer end of said plunger and engageable with said rearward portion.

11. A tampon applicator comprising:
a tubular barrel adapted to house and carry a tampon therein and a slidable, tubular plunger telescopically engageable with said barrel and operable to push the innermost end of the tampon within the barrel out of the forward end of the barrel into a vagina;
said tubular barrel comprising:
(a) a cylindrical front portion adapted to house said tampon;
(b) a rearward portion adapted to partially house and engage said plunger, said rearward portion of said barrel comprising:
two diametrically opposed, substantially flattened surfaces with a plurality of spaced apart ribs, and
two diametrically opposed, angled shoulder surfaces;
whereby said flattened surfaces and said angled surfaces provide a finger and thumb hold enabling a user to comfortably eject and control the position of said tampon.

12. The applicator of claim 11 further comprising means for guiding said plunger axially within said rearward portion, said guide means comprising a plurality of protrusions on an inner tubular surface of said rearward portion of said barrel which are axially engageable with said outer tubular surface of said plunger.

13. The applicator of claim 11 wherein said flattened surfaces of said barrel comprises an arcuate depression.

14. The applicator of claim 11 further comprising means for limiting the movement of said plunger through said rearward portion, said limiting means comprising a first curled lip integral with the inner end of said plunger and engageable with said angled surfaces and a second curled lip integral with the outer end of said plunger and engageable with the outer end of said flattened surfaces of said rearward portion.

* * * * *